United States Patent
Pralong

(10) Patent No.: US 10,010,916 B2
(45) Date of Patent: Jul. 3, 2018

(54) MEASURING THERMAL EXPANSION AND THE THERMAL CROWN OF ROLLS

(71) Applicant: NOVELIS INC., Atlanta, GA (US)

(72) Inventor: Antoine Jean Willy Pralong, Granges (CH)

(73) Assignee: NOVELIS INC., Atlanta, GA (US)

(*) Notice: Subject to any disclaimer, the term of this patent is extended or adjusted under 35 U.S.C. 154(b) by 0 days.

(21) Appl. No.: 14/203,695

(22) Filed: Mar. 11, 2014

(65) Prior Publication Data
US 2014/0260474 A1  Sep. 18, 2014

Related U.S. Application Data

(60) Provisional application No. 61/776,925, filed on Mar. 12, 2013.

(51) Int. Cl.
| | |
|---|---|
| *B21B 38/00* | (2006.01) |
| *B21B 37/74* | (2006.01) |
| *B21B 38/12* | (2006.01) |
| *G01N 25/16* | (2006.01) |

(52) U.S. Cl.
CPC ............ *B21B 38/00* (2013.01); *B21B 37/74* (2013.01); *B21B 38/12* (2013.01); *G01N 25/16* (2013.01); *B21B 2267/06* (2013.01); *B21B 2267/19* (2013.01)

(58) Field of Classification Search
CPC ........ G01N 25/16; G01N 29/02; G01N 29/00; G01N 29/04; G01N 29/12; B21B 37/28; B21B 28/04; B21B 13/023; B21B 37/74; B21B 38/12; B21B 38/00
See application file for complete search history.

(56) References Cited

U.S. PATENT DOCUMENTS

| | | | | |
|---|---|---|---|---|
| 4,976,149 A | * | 12/1990 | Ichikawa | ............... B21B 38/12 367/104 |
| 5,212,975 A | * | 5/1993 | Ginzburg | ............... B21B 27/10 239/562 |
| 5,392,123 A | | 2/1995 | Marcus et al. | |

(Continued)

FOREIGN PATENT DOCUMENTS

| | | |
|---|---|---|
| CN | 102706317 A | 10/2012 |
| DE | 102006028369 A1 | 12/2007 |

(Continued)

OTHER PUBLICATIONS

Copy from EAST for JP02223814A.*

(Continued)

*Primary Examiner* — Peter DungBa Vo
*Assistant Examiner* — John S Lowe
(74) *Attorney, Agent, or Firm* — Kilpatrick Townsend & Stockton LLP

(57) ABSTRACT

Systems and methods for measuring the thermal crown of rolls in-situ (e.g., at high temperature) either inside or outside the rolling mill can include sensors that measure propagation times of mechanical waves through the rolls. In some embodiments, one or more sensors are used to measure the propagation times of ultrasonic waves traveling inside the roll and normal to the roll's axis. These measurements can be taken when the roll is still hot and can be used to determine in real-time the thermal expansion at various points along the roll.

12 Claims, 6 Drawing Sheets

(56) References Cited

U.S. PATENT DOCUMENTS

| | | | |
|---|---|---|---|
| 5,581,351 A * | 12/1996 | Marcus | G01B 11/14 356/625 |
| 5,918,493 A | 7/1999 | Cerv | |
| 5,945,595 A | 8/1999 | Mori et al. | |
| 6,014,881 A | 1/2000 | Imanari | |
| 7,987,719 B2 | 8/2011 | Stuber et al. | |
| 8,490,490 B2 | 7/2013 | Yamano | |
| 8,639,488 B2 | 1/2014 | Volker et al. | |
| 2004/0085550 A1 | 5/2004 | Okuno et al. | |
| 2006/0075817 A1* | 4/2006 | Yuhas | F41A 31/02 73/598 |

FOREIGN PATENT DOCUMENTS

| | | | |
|---|---|---|---|
| EP | 0221785 | A2 | 5/1987 |
| EP | 542640 | A1 | 5/1993 |
| EP | 779112 | A1 | 6/1997 |
| EP | 1216766 | A2 | 6/2002 |
| EP | 1185385 | B1 | 9/2003 |
| EP | 1120628 | B1 | 8/2005 |
| JP | S61099520 | A | 5/1986 |
| JP | 02223814 | A * | 9/1990 |
| JP | 04292365 | A | 10/1992 |
| JP | H06087013 | A | 11/1994 |
| JP | 08136516 | A * | 5/1996 |
| JP | H08136516 | A | 5/1996 |
| JP | H10176998 | A | 6/1998 |
| JP | 2001116733 | A | 4/2001 |
| JP | 2001205312 | A | 7/2001 |
| JP | 2004157114 | A | 6/2004 |
| JP | 2010181174 | A | 8/2010 |
| JP | 2011002279 | A | 1/2011 |

OTHER PUBLICATIONS

Merged document with English abstract of JP02223814A to Adachi.*
Machine translation JP08136516A to Sanpei; May 1996.*
Original document with merged abstract JP 08136516 A to Sanpei; May 1996.*
Machine translation JP02223814A to Adachi; Sep. 1990.*
Original document with merged abstract JP02223814A to Adachi; Sep. 1990.*
International Patent Application No. PCT/US2014/022972, International Search Report and Written Opinion dated Jun. 10, 2014, 9 pages.
Montmitonnet, Pierre, "Hot and cold strip rolling processes", Comput. Methods Appl. Mech. Engrg., 2006, pp. 6604-6625, vol. 195, Elsevier, 2006, 22 pages.
Moore, J. M., "Measurement of Work Rolled Profile During the Rolling Process", Technical Steel Research, 1987, Commission of the European Communities, 97 pages.
Chinese Patent Application No. 201480009953.2, Office Action dated May 23, 2016, 16 pages.
Canadian Patent Application No. 2,901,195, Office Action dated Oct. 17, 2016, 3 pages.
Korean Patent Application No. 10-2015-7028525, Office Action dated Dec. 1, 2016, 6 pages.
European Patent Application No. 16182740.7, Extended European Search Report dated Dec. 7, 2016, 8 pages.
Japanese Patent Application No. 2016-501114, Office Action dated Feb. 21, 2017, 8 pages.
European Patent Application No. 14714884.5, Office Action dated Apr. 18, 2017, 3 pages.
European Patent Application No. 14 714 884.5, Office Action dated Sep. 19, 2016, 4 pages.
Korean Patent Application No. 10-2015-7028525, Second Office Action dated Jul. 3, 2017, 11 pages.
Japanese Patent Application No. 2016-501114, Office Action dated Oct. 17, 2017, 8 pages.
Korean Patent Application No. 10-2015-7028525, Office Action dated Dec. 22, 2017, 5 pages.
Korean Patent Application No. 10-2015-7028525, Office Action dated Mar. 27, 2018, 7 pages.

* cited by examiner

MEASURING THERMAL EXPANSION AND THE THERMAL CROWN OF ROLLS

CROSS REFERENCE TO RELATED APPLICATIONS

The present application claims the benefit of U.S. Provisional Patent Application Ser. No. 61/776,925 filed Mar. 12, 2013, which is hereby incorporated by reference in its entirety.

TECHNICAL FIELD

The present application relates to systems and methods for measuring the thermal expansion and thermal crown of rolls in-situ.

BACKGROUND

Rolling is a metal forming process in which stock sheets or strips are passed through a pair of rolls to reduce the thickness of the stock sheets or strips. Due to the high temperatures generated from the friction of rolling, from material deformation, and/or from contacting hot incoming material, the rolls may experience thermal expansion (also referred to as thermal crown). Thermal expansion along the roll axis is referred to as the thermal crown and the average in thermal expansion along the roll axis is referred to as the thermal expansion. Accurate measurements of the thermal expansion/crown of the roll when the roll is hot are needed for many reasons, one of which is to ensure that proper adjustments are made when needed to position the rolls properly relative to the strips to ensure that the rolled metal strips are of the desired flatness and profile.

Because of the high roll temperatures and the environment of a mill, however, it is difficult to measure the profile/camber of the rolls at the required time during the rolling process. Numerical models are therefore used to simulate the evolution of the thermal expansion and thermal crown of the roll by estimating the initial conditions and the heat transfer at the roll surface. Although these numerical models do not require direct measurements, the results are limited in accuracy because of the difficulty of accurately estimating the model parameters. In some cases, thermal crown is inferred using flatness or profile measurements of the strip as it exits the roll bite, but such methods are of limited accuracy and are only useful if the entry profile of the sheet is known accurately, the mill is a single stand mill, and the mill is running. These methods also only apply to the portion of the roll in contact with the strip, and so the thermal crown of the roll located outside the strip must be estimated. In a similar way, the thermal expansion can be inferred using the measured exit strip thickness, but limitations similar to those associated with the inferred crown method also exist.

Other attempts at measuring the thermal crown of a roll involve measuring the distance between a sensor and a roll, which also has limitations. For instance, the beam upon which such sensors are mounted may deform, rendering the sensors inaccurate. Efforts to minimize beam deformation or compensate for beam deformation can be cumbersome (e.g., occupy a significant amount of space on/near the machinery) and expensive.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Systems and methods are disclosed for measuring the thermal expansion and/or thermal crown of rolls either inside or outside a rolling mill. In some embodiments, the measurement is obtained by measuring the change in propagation time of an ultrasound wave traveling inside the roll when the roll is at different temperatures. Some measurements are capable of being made while the rolls are at high temperatures.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
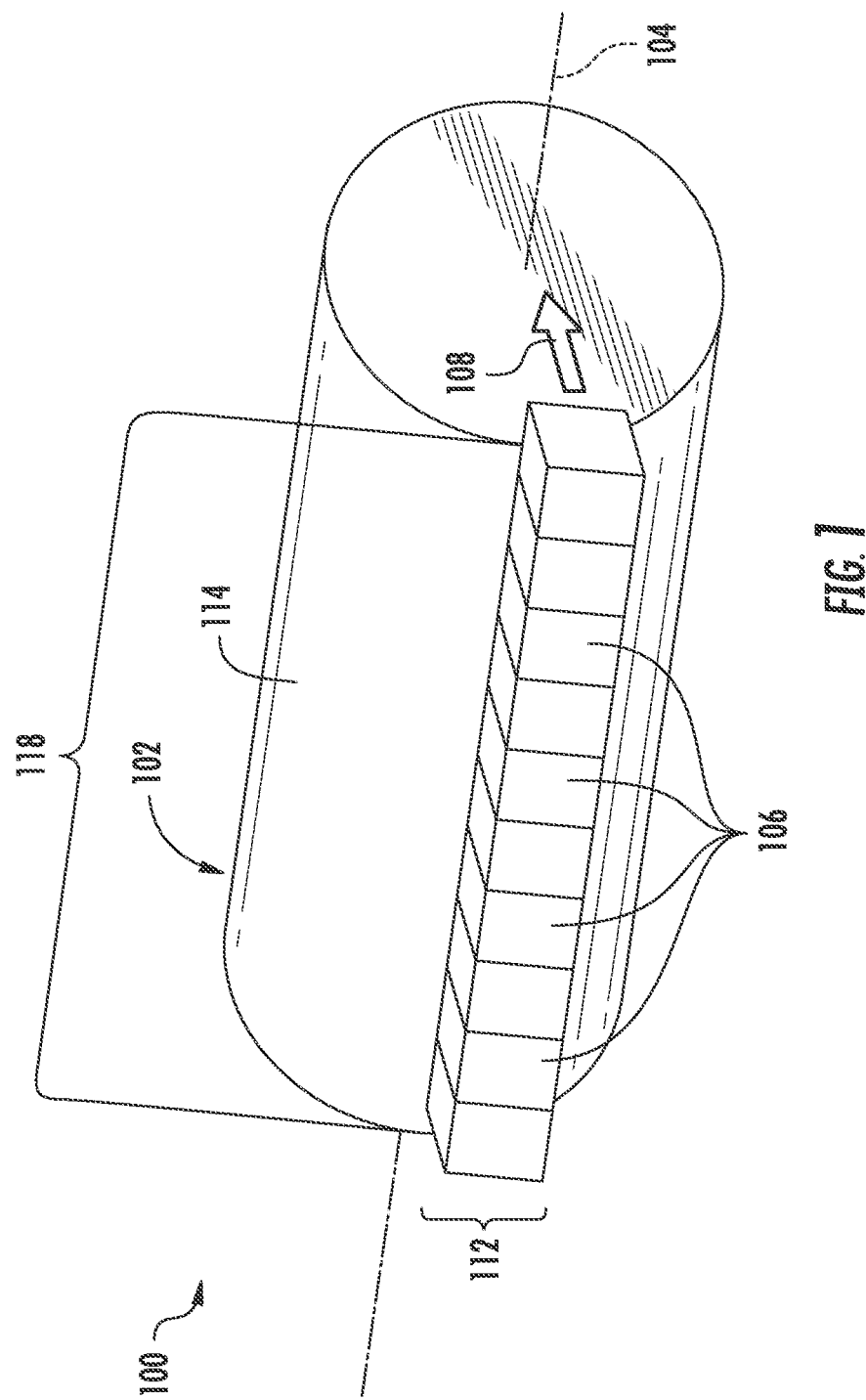
FIG. 1 is an isometric view of a roll including a sensor.

Systems and processes are disclosed for directly measuring the thermal expansion of a roll, such as a metalworking roll, while the roll is hot. Thermal expansion is calculated by comparing propagation times of ultrasound waves within the roll while cold with propagation times of ultrasound waves within the roll while hot. As used herein, the term "thermal expansion" includes both positive and negative thermal expansion, such as thermal expansion and thermal contraction, where appropriate.

Measuring thermal expansion of a roll in situ (i.e., in the mill), when the rolls are hot, can enable accurate and dynamic control of the effects of thermal expansion. Specifically, it can be advantageous to control the effects of thermal crown. Obtaining an accurate measurement of the thermal expansion of the rolls in situ has many applications. For example, obtaining an accurate measurement of thermal expansion in situ when the roll is hot allows for precise adjustment of the mill setup and/or the roll cooling or heating (using actuators or otherwise). Accurate measurements of thermal expansion can enable reduction in the cool back times between product changes. Accurate measurements of thermal expansion can improve the thickness/profile of the product (e.g., a sheet of metal), as well as flatness such as edge tension in cold rolling. Accurate measurements of thermal expansion can improve the accuracy of thermal models or roll expansion and crown.

More particularly, obtaining direct measurements of the thermal expansion can be used, for example, to: (1) calculate a more accurate roll gap gauge presetting (i.e., roll gap space before the strip is introduced to the mill) so that the thickness target for the strip is achieved more quickly; (2) calculate a better roll bending presetting (i.e., roll gap space distribution across the width before the strip is introduced to the mill) so that the flatness/profile target of the strip is achieved more quickly; (3) generate better estimates of strip gauge between the stands of a multi-stand mill to improve overall speed/thickness; and (4) generate better estimates of the strip thickness profile between the stands of a multi-stand mill to improve overall flatness and/or profile.

Additionally, thermal expansion measurements can be used to quantify the variation of thermal expansion over one rotation of the roll, which can be used to assess the amount of thermal induced eccentricity. Measurements of the thermal induced eccentricity can be used to determine online when the mill is ready for rolling without inducing eccentricity-induced gauge variations after a forced outage or an emergency stop. Measurements of the thermal induced eccentricity can also be exploited by measuring each roll in the roll stack to quantify the amount of thermal eccentricity versus mechanical eccentricity when overall eccentricity is measured using standard mill sensors such as roll stand loads. These measurements, when associated with mill vibration measurements, can help to interpret vibration spectra and monitor machine condition and/or predict component failure (predictive maintenance) such as roll bearings.

Moreover, the thermal expansion measurements can be used to optimize coolant temperature and monitor the condition of roll cooling sprays for feedback control, spray optimization, thermal model optimization, and other purposes.

Obtaining accurate thermal expansion measurements can dynamically improve the accuracy of online rolling models and can be used to help make dynamic adjustments to the rolling process, as discussed above.

In some cases, the thermal expansion, crown and/or eccentricity of the work rolls is measured. In other cases, the thermal expansion, crown and/or eccentricity of intermediate and/or backup rolls is also measured.

The embodiments disclosed herein can provide for measurement of thermal expansion, crown and eccentricity with more accuracy and with less cost than other methods.

The systems and methods disclosed herein are not limited to use in rolling, but can be applied to any process or application where it is desirable to measure a dimensional change due to a thermal variation. In addition, the disclosed systems and methods can be used to calculate thermal contraction of a roll being cooled.

These illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure. The elements included in the illustrations herein may be drawn not to scale.

FIG. 1 is an isometric view of a metalworking system 100 including roll 102 and a sensor bar 112. The sensor bar 112 can include one or more individual sensors 106. The roll 102 has a longitudinal axis 104 extending longitudinally through the center of the roll 102. The longitudinal axis 104 is also known as the rotational axis. The roll 102 has an exterior surface 114.

Each sensor 106 can include one or more individual devices capable of transmitting and/or receiving ultrasound waves 108. In some embodiments, a sensor 106 can be an ultrasound sensor, a phased array sensor, a shock generator, a piezoelectric transducer, a device for electromagnetic induction/measurement of mechanical waves (e.g., an electromagnetic acoustic transducer (EMAT)), a laser, or another device suitable for generating and/or measuring a mechanical wave. Each sensor 106 can include one or more transducers. In some cases, sensor 106 is an ultrasonic sensor that operates at relatively low frequencies, such as between approximately 0.5 and 10 MHz. In one non-limiting embodiment, the sensor 106 is a piezoelectric 0.5 MHz 1 inch diameter ultrasound sensor and in another is a piezoelectric 10 MHz 0.5 inch diameter ultrasound sensor.

While the present disclosure often refers to ultrasound waves 108, other mechanical waves capable of propagating through the roll 102 can be used instead.

As depicted in FIGS. 2-5, the mechanical wave 108 shown is also an indication of the wave path that the mechanical wave 108 travels.

As shown in the embodiment of FIG. 1, one or more sensors 106 are positioned at one or more fixed locations, longitudinally spaced along the width of the roll 102. Each sensor takes measurements at the sensor's 106 respective location, as described in further detail below.

In alternate embodiments, one or more sensors 106 traverse longitudinally along the width 118 of the roll 102 such that measurements are taken at a plurality of locations longitudinally spaced along the width 118 of the roll 102, as described in further detail below.

Regardless of the type of measurement system 214 used, the system 100 can use information obtained from the one or more sensors 106, the position of the sensors relative to the roll width 118, and the angular position of the sensors relative to the roll 102 to construct a three dimensional model of the thermal expansion, crown, and eccentricity of the roll. In some embodiments, rapid time-variable cooling could then be used to adjust the roll shape in a circumferential direction to control for eccentricity or otherwise. In other embodiments, distributed cooling along the roll width 118 can be applied to bring the effective thermal crown of the roll 102 to a target value. In other embodiments, overall cooling can be controlled to change the effective thermal expansion of the roll 102 to its target value.

Figure 2:
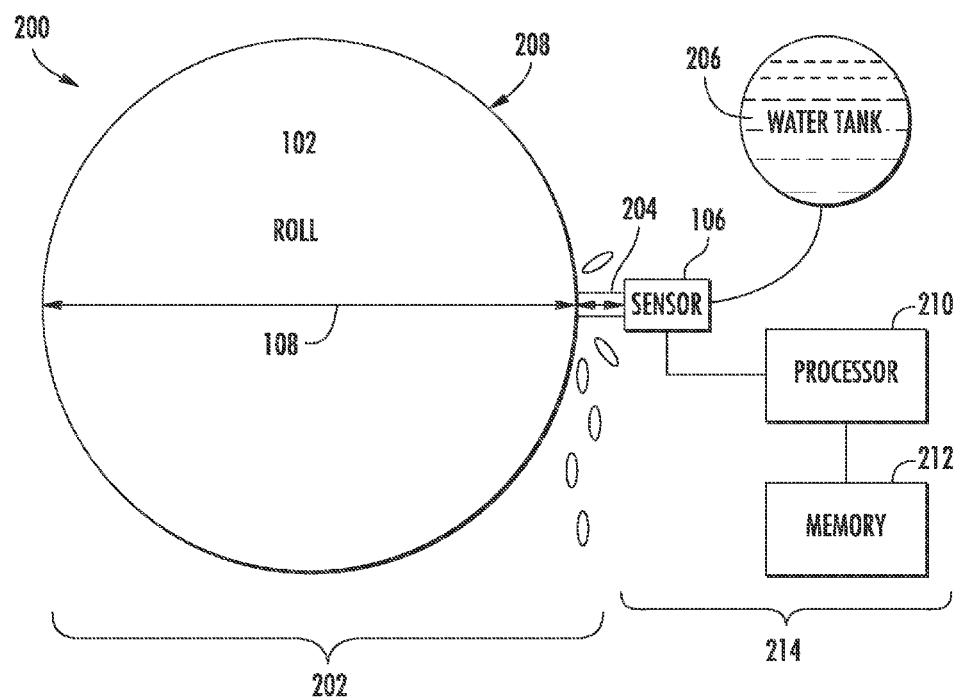
FIG. 2 is a schematic end view of a roll positioned relative to a sensor.

FIG. 2 is a schematic end view of a system 200 including a roll 102 positioned relative to a sensor 106. The sensor 106 shown in FIG. 2 includes one or more transducers capable of transmitting and/or receiving a wave 108. The transducer or other mechanism for generating and/or transmitting the wave 108 may be part of the sensor 106, or may be separate from the sensor 106. The sensor 106 can be operatively connected to a processor 210 for performing data acquisition, data processing, and the calculations disclosed herein. The processor 210 can be operatively connected to a memory 212 for storing measurements, as disclosed below.

The sensor 106, processor 210, and memory 212 can be considered components of a measurement system 214.

In some embodiments, a wave coupling 204 is positioned between a sensor 106 and the roll 102. The coupling 204 can be water, an emulsion, a gel, or any other suitable material or mechanism that acts as a medium for the wave 108 to propagate between the sensor and the surface 208 of the roll 102. If the wave coupling 204 is a water coupling, a water tank 206 can be used to supply water to the water coupling. For a single transmitter-receiver sensor, the dimension of the coupling layer (in the direction of the ultrasonic wave) is chosen such that the echoes from the roll-coupling interface do not interfere with the echoes from the rear side of the roll.

The system 100 (e.g., at least sensor 106 and processor 210) is configured to measure how long it takes a wave 108 to propagate inside the roll 102 in a direction substantially normal to the longitudinal axis 104 of the roll 102. As used herein, a direction substantially normal to the longitudinal axis 104 can be a direction following a line that falls within a plane substantially normal to the longitudinal axis 104, where the line can, but does not necessarily, intersect the longitudinal axis 104. The propagation time measurement in turn can be used as explained below to calculate the thermal expansion of the roll 102 at a particular point along the width of the roll 102. The propagation time of a wave 108 is sometimes referred to as a flight time, and refers to the time it takes for the wave 108 to propagate between a transmitter and a receiver or through a body (e.g., a roll 102). In some cases, the wave 108 undergoes one or multiple reflections inside the roll 102.

Thermal expansion of a roll 102 is determined by measuring the change in propagation time of a wave 108 when the roll 102 is at a reference temperature $T_R$ (e.g., room temperature) and at the rolling temperature $T_H$ (e.g., "in situ" temperature or "hot" temperature, as used herein). In some cases, the propagation time of the wave 108 is measured as the wave propagates through the roll 102, substantially normal to the longitudinal axis 104, and across the roll diameter 202 (FIG. 2).

The propagation time of a wave 108 propagating through a roll 102 depends on both the roll diameter 202 and the speed of sound c. Both the roll diameter 202 and the speed of sound c depend on roll temperature. As used herein, $t_R$ is the propagation time of the wave 108 through the roll 102 when the roll 102 is at the reference temperature $T_R$ and $t_H$ is the propagation time of the wave 108 through the roll 102 when the roll 102 is at the in situ temperature $T_H$. As used herein, $t_R$ can be referred to as a "reference propagation time measurement" and $t_H$ can be referred to as a "in situ propagation time measurement." As used herein, $Ø_R$ is the roll diameter 202 when the roll 102 is at reference temperature and $Ø_H$ is the roll diameter 202 when the roll 102 is at the in situ temperature. For instance, a roll can be at reference temperature $T_R$ when the roll is at a location remote from the rolling mill, or just after a roll change when the new roll is in the mill, but rolling has not started. In some embodiments, the in situ measurements are taken using the same sensor 106 taking the reference measurements. In alternate embodiments, the in situ measurements are taken using one or more different sensors 106 than those taking the reference measurements.

The change in propagation time Δt of the wave 108 from the reference thermal state (e.g., roll 102 at $T_R$) to the in situ state (e.g., roll 102 at $T_H$) can be correlated to the change in temperature ΔT (where $ΔT=T_H-T_R$). The change in propagation time Δt can be correlated to thermal expansion (i.e., the change in roll diameter ΔØ) and ultimately the diameter $Ø_H$ along the hot roll, as described herein.

Equation 1, below, can be used to relate the change in roll diameter ($ΔØ=Ø_H-Ø_R$) due to a change in thermal state (ΔT) to the change in propagation time ($Δt=t_H-t_R$) of the ultrasonic wave due to the same change in thermal state (ΔT).

$$ΔØ = β\frac{c}{2n}Δt \text{ assuming } \left|\frac{Δt}{t_R}\left(1-\frac{1}{β}\right)\right| \ll 1 \qquad \text{Equation 1}$$

In Equation 1, ΔØ is the change in roll diameter, c is the speed of sound at the reference temperature $T_R$ (e.g., at room temperature), n is the number of echoes inside the roll 102, Δt is the change in propagation time of the wave between the reference temperature $T_R$ and the in situ temperature $T_H$ (i.e., $Δt=t_H-t_R$), and $t_R$ is the propagation time at the reference temperature ($T_R$) (in some cases, room temperature). β is a material parameter that depends on α, the thermal expansion coefficient of the material of roll 102, and dc/dT, the change in sound speed with temperature, as seen in Equation 2, below.

$$β = \frac{1}{1+\frac{-dc/dT}{αc}} \qquad \text{Equation 2}$$

The factor β can be determined once for a given roll 102 (or a set of rolls with the same or substantially the same material properties).

A change in diameter ΔØ between the reference temperature $T_R$ and the in situ temperature $T_H$ can be calculated. A reference propagation time measurement $t_R$ of the roll diameter 202 can be made at the reference temperature $T_R$ (e.g., at a location remote from the rolling mill) at any location along the width of the roll 102. The reference propagation time measurement $t_R$ can be stored in memory 212. An in situ propagation time measurement $t_H$ can be made at the in situ temperature $T_H$ at various points along the width of the roll 102. The change in diameter ΔØ at each of these various points can be calculated according to Equation 1, above. The roll diameter at in situ temperature (hereinafter $Ø_H$) at each of these various points can be inferred by adding the calculated change in roll diameter ΔØ to a reference measurement of the roll diameter $Ø_R$ at the reference temperature. The reference measurement of the roll diameter $Ø_R$ can be made using known techniques. The reference measurement of the roll diameter $Ø_R$ can be stored in memory 212.

The disclosed calculation using a change in propagation time Δt of a wave 108 is not limited to use in rolling applications, but can be used in any application or process where it is desirable to obtain the thermal expansion of any body.

Moreover, the principles described herein can be used to measure the thermal contraction of a roll 102 or any body according to the same principle, but with a reference temperature hotter than the in situ temperature (i.e., $T_R > T_H$).

Propagation times (e.g., $t_R$ and $t_H$) can be measured using a single wave, an average of multiple waves propagating along a unique path, or an average of multiple waves propagating along multiple paths. For example, propagation times measured using an average of multiple waves propagating along multiple paths can be the average propagation time of waves passing through multiple diameters 202 of the roll 102, where each diameter 202 is located in the same plane normal to the roll axis 104. In other words, the multiple diameters 202 can be measured from various points along the circumference of the roll 102 in order to build an average propagation time in a particular plane. In other embodiments, the change in roll diameter ΔØ or the roll diameter $Ø_H$ can be averaged.

Figure 3:
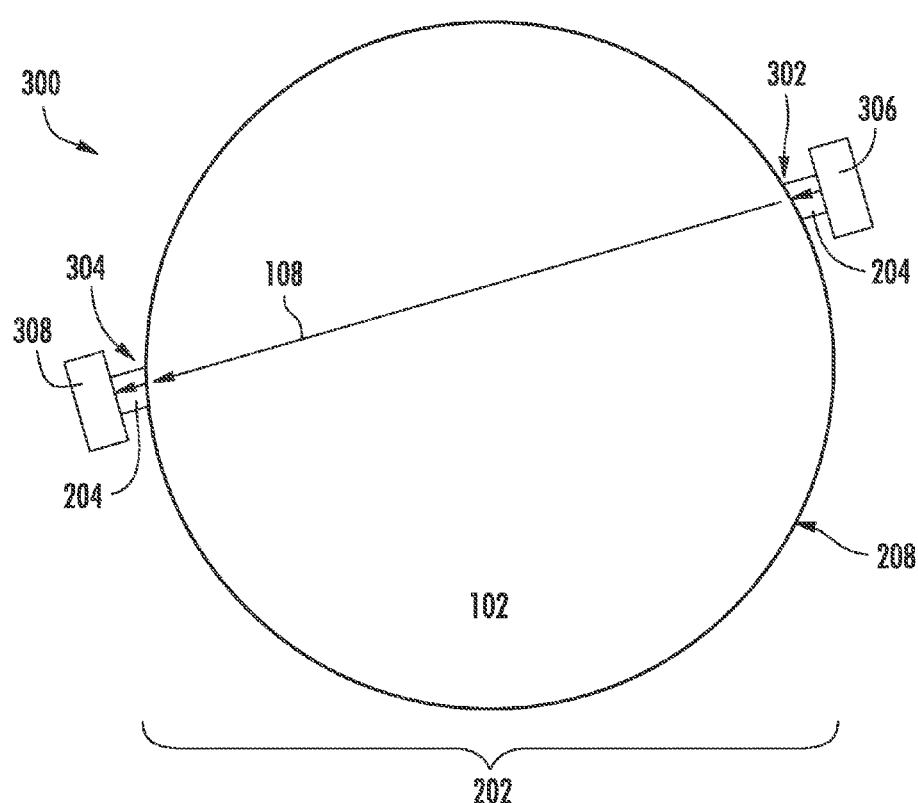
FIG. 3 is a schematic end view of a roll including a wave generator transmitting a wave from a first location to a sensor at a second location.

FIG. 3 is a cross-sectional view of a system 300 including a roll 102. Travel of the wave 108 need not to follow the entire diameter 202 of the roll 102. The wave 108 can follow any chord which is meaningful for inferring a thermal expansion. The wave 108 does not need to travel in a direction normal to the longitudinal axis 104, but can take any direction. The formula of the thermal expansion can then be adapted by geometrical considerations.

Any reflection occurring inside the roll 102 can be exploited as well to calculate a thermal expansion, including reflections from an internal interface (e.g., an internal acoustic interface). The formula of the thermal expansion can then be adapted using geometrical considerations.

In some embodiments, a wave 108 is generated and measured at approximately the same location on the surface 208 of the roll 102 after the wave 108 reflects off of an inside surface 402 of the roll 102 (e.g., wave 108 reflecting off inner surface 402 in FIG. 4, as described in further detail below). In other embodiments the configuration is similar to FIG. 4 but the sensor is located in the hole 404 of the roll 102. In other embodiments, a wave 108 is generated and measured at approximately at the same location on the surface 208 of the roll 102 after the wave 108 followed some chord of the roll (e.g., the wave 108 reflecting off surface 208 of FIG. 5, as described in further detail below). In alternate embodiments, as shown in FIG. 3, a wave 108 is generated at a first location 302 by a transmitter 306 and measured at a second location 304 by a receiver 308. The first location 302 and/or the second location 304 can be on the surface 208 of the roll 102, within the roll 102, or located outside the roll. In some cases, the wave 108 undergoes one or multiple reflections before reaching the second location 304.

As seen in FIG. 3, the transmitter 306 is positioned opposite receiver 307 along a secant of the roll 102 intersecting the receiver 307. In other words, the receiver 307 can be positioned along a line collinear with a chord of the roll and intersecting the transmitter in order to measure waves that follow that chord of the roll. In other embodiments, the transmitter 306 and the receiver 307 may be positioned at any suitable locations along roll 102.

Figure 4:
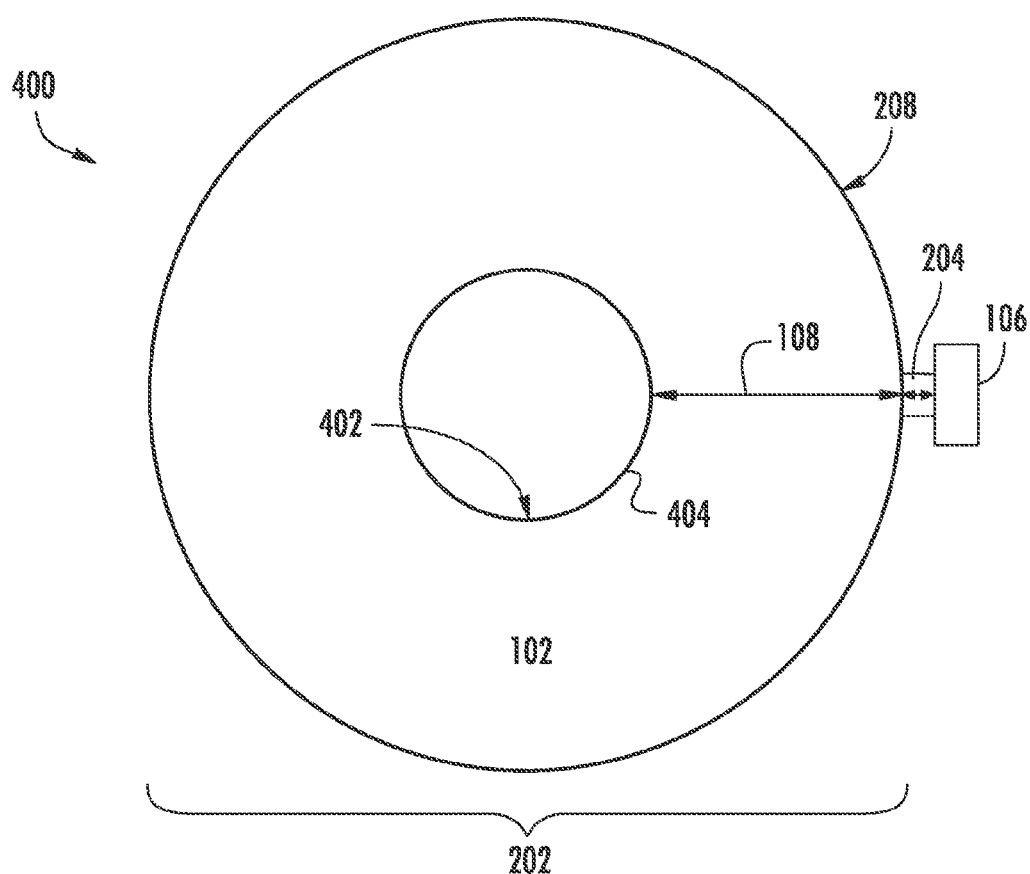
FIG. 4 is a schematic end view of a hollow roll including a sensor.
Figure 5:
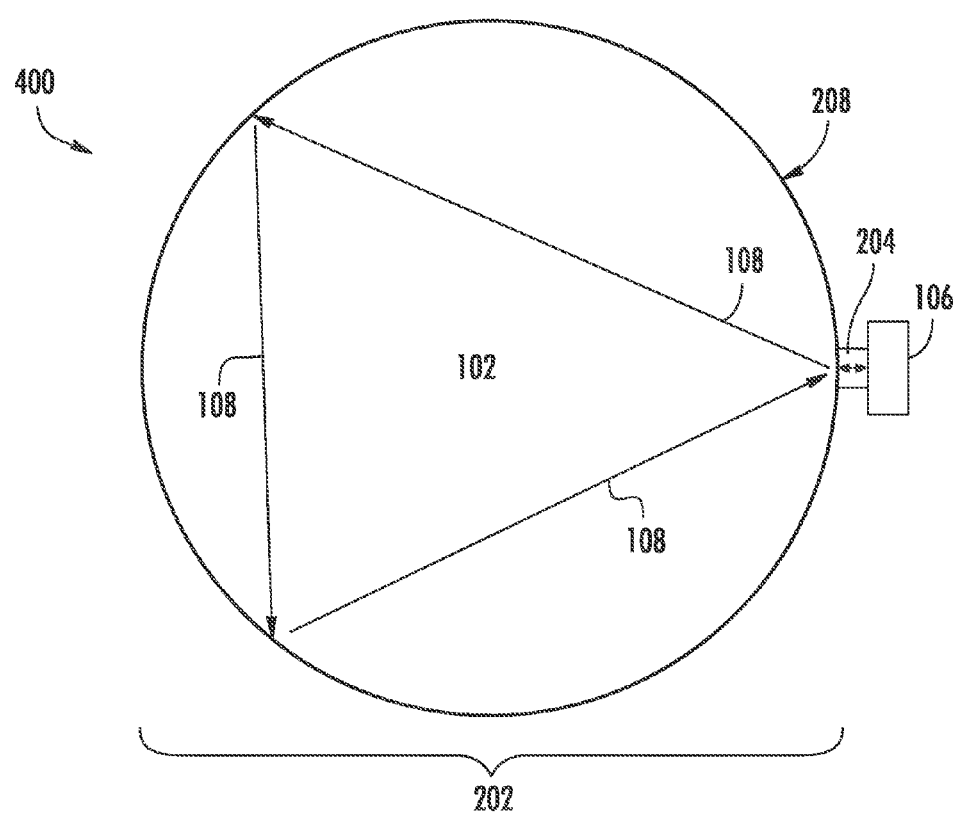
FIG. 5 is a schematic end view of a roll with a wave starting and arriving at the same point without following the roll diameter.

FIG. 4 is a cross-sectional view of a hollow roll 102 having a hole 404. Hole 404 need not be centered and need not be round as illustrated. The sensor 106 can measure the propagation time of a wave 108 as it travels through the roll 102 and is reflected off the inner surface 402 of the roll 102. The average diameter of the hole 404 can be calculated as the roll 102 makes a full rotation. When the hole 404 is eccentric, the average diameter can be used to determine the distance the wave 108 propagates through the roll 102.

Figure 6:
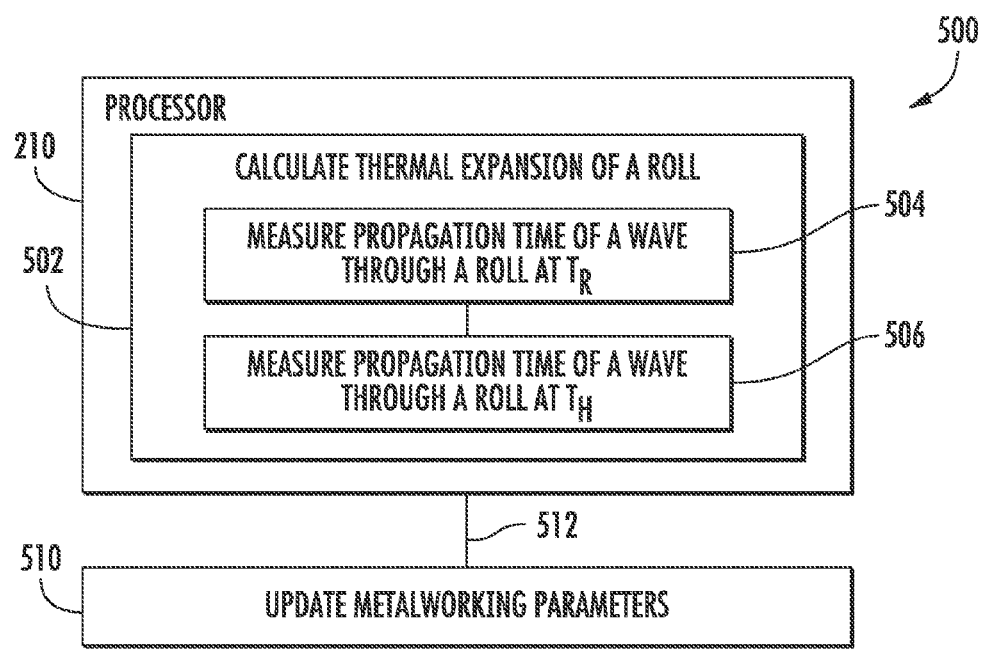
FIG. 6 is a flowchart of an exemplary method of measuring thermal crown.

FIG. 6 is a flowchart of a method of measuring thermal expansion and using the measured thermal expansions to make any desired adjustments according to one embodiment 500. In a processor 210, thermal expansion of a roll 102 is calculated at block 502. Block 502 includes measuring the propagation time of a wave through a roll at $T_R$ at block 504 and measuring the propagation time of a wave through a roll at $T_H$ at block 506. The thermal expansion data 512 can be used to update metalworking parameters at block 510. Metalworking parameters can include any setting or adjustment used in the metalworking process, including parameters for improving mill setup adjustment, optimization of cool back time, improving control of heat transfer from/to rolls, improving the thermal model (e.g., more frequent re-calibration), improving strip thickness control, improving strip profile control, improving strip flatness control, improving roll eccentricity compensation, and others.

Figure 7A:
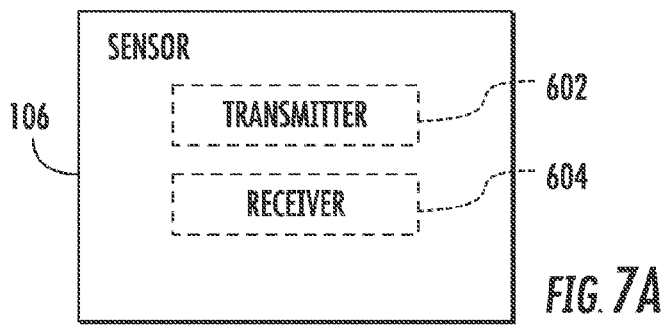
FIG. 7A is a schematic view of a sensor having a transmitter and a receiver according to one embodiment.

FIG. 7A is a schematic illustration of a sensor 106 according to one embodiment. As used herein, a sensor 106 can include both a transmitter 602 and a receiver 604. In alternate embodiments, a sensor 106 can include only a transmitter 602. In alternate embodiments, a sensor 106 can include only a receiver 604. A transmitter 602 is any device capable of producing waves 108, such as those described in further detail above. A receiver 604 is any device capable of measuring a wave 108 propagating/reflecting on the receiver 604, such as those described in further detail above. In embodiments where a sensor 106 includes both a transmitter 602 and a receiver 604, the transmitter 602 and receiver 604 can be a single device or two separate devices co-located in a single housing.

Figure 7B:
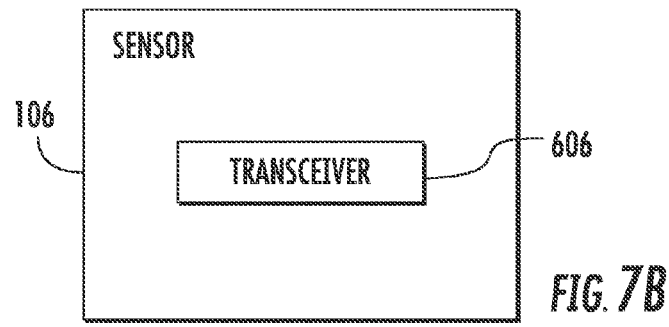
FIG. 7B is a schematic view of a sensor having a transceiver according to one embodiment.

FIG. 7B is a schematic illustration of a sensor 106 according to one embodiment. In this embodiment, the sensor 106 includes a transceiver 606 capable of both transmitting and receiving waves 108.

In some embodiments, waves 108 can further include, but not be limited to, longitudinal and traverse waves or surface waves (to measure surface temperature and roll circumference).

As discussed above, measuring the thermal crown of rolls has many potential applications. In one embodiment, average roll temperature ($T_{Avg}$) can be inferred according to Equation 3, below.

$$T_{Avg} = \frac{\beta}{\alpha}\frac{\Delta t}{t_R} + T_R \text{ assuming } \left|\frac{\Delta t}{t_R}\left(1 - \frac{1}{\beta}\right)\right| \ll 1 \qquad \text{Equation 3}$$

Equation 3 or other equations using the change in propagation time (Δt) of a wave are not limited to use in rolling applications, but can be used in any application or process where it is desirable to obtain the temperature of any body (e.g., $T_{Avg}$). Inferring the temperature of a roll 102 can help, for example, obtain a more accurate cooling model. A cooling model can be any mathematical formulation relating some parameters (e.g., parameters for actuators controlling water cooling flow, pressure distribution, or heating devices) to the temperature of the roll. From the average roll temperature ($T_{Avg}$) and the reference temperature ($T_R$), the thermal expansion can be inferred using the thermal expansion coefficient (α).

The average roll surface temperature can be inferred from the change in travel time of a surface wave traveling along the roll circumference in a similar way as the average roll temperature measurement.

Assuming a steady thermal state, the difference in the thermal expansion (e.g. thermal crown) measured with and without rolling load can be exploited using acoustoelasticity to calculate the stress distribution inside the roll.

The change in roll diameter ΔØ or roll temperature ΔT can be calculated using only measurements of waves 108 propagating in a roll 102. There is no need for external temperature measurement devices or additional distance-measuring devices. Accurate calculations of thermal expansion and change in temperature of a roll 102 can be made using only two measurements: $t_R$ and $t_H$.

Table 1 is a reference of symbols used throughout this disclosure. The meaning of each symbol is listed below for reference and shall not be limiting in nature.

TABLE 1

| Symbol | Meaning |
|---|---|
| $T_R$ | Reference temperature (e.g., room temperature) |
| $T_H$ | In situ temperature (e.g., hot temperature of a roll in use) |
| $\Delta T$ | Change in temperature between $T_H$ and $T_R$ |
| $t_R$ | Propagation time of a wave through a roll at $T_R$ |
| $t_H$ | Propagation time of a wave through a roll at $T_H$ |
| $\Delta t$ | Change in propagation time of the wave between $T_R$ and $T_H$ |
| $\Delta \varnothing$ | Change in roll diameter |
| $\varnothing_H$ | Roll diameter at $T_H$ |
| $\varnothing_R$ | Roll diameter at $T_R$ |
| c | Speed of sound at $T_R$ |
| n | Number of echoes inside the roll |
| α | Thermal expansion coefficient of the material of the roll |
| β | A material parameter that depends on α and dc/dT |
| $\frac{dc}{dT}$ | Change in sound speed with temperature |
| $T_{Avg}$ | Average roll temperature |

All patents, publications and abstracts cited above are incorporated herein by reference in their entirety. Various embodiments have been described. These embodiments are presented only for the purpose of illustration and description and are not intended to be exhaustive or limiting to the precise forms disclosed. Numerous modifications and adaptations thereof will be readily apparent to those skilled in the art.

What is claimed is:

1. A method for measuring thermal expansion of a roll having a diameter and a surface comprising:
   determining a reference propagation time of a reference mechanical wave propagating along at least one of the diameter or a chord of the roll and through the roll at a reference temperature of the roll, wherein the reference mechanical wave is transmitted through a coupling positioned between a sensor and the roll in a direction that lies within a plane that is normal to an axis of rotation of the roll and wherein the reference propagation time of the reference mechanical wave depends on the reference temperature of the roll;
   transmitting an in situ mechanical wave at a first location on the surface and across at least one of the diameter or the chord and through the roll at an in situ temperature of the roll, the roll rotating about an axis of rotation, wherein the in situ mechanical wave is transmitted through the coupling in a direction that lies within a plane that is normal the axis of rotation during rotation of the roll;
   measuring an in situ propagation time of the in situ mechanical wave through the roll at a second location, wherein the in situ propagation time of the in situ mechanical wave depends on the in situ temperature of the roll; and
   determining an amount of thermal expansion of the roll, through which the reference mechanical wave and the in situ mechanical wave pass, between the reference temperature and the in situ temperature by comparing the in situ propagation time with the reference propagation time.

2. The method of claim 1, wherein:
   the in situ mechanical wave is transmitted by a transmitter and measured by a receiver; and
   the reference mechanical wave is transmitted by the transmitter and measured by the receiver.

3. The method of claim 1, wherein the body is a roll for metalworking.

4. The method of claim 3, wherein each of the in situ mechanical wave and the reference mechanical wave propagates along the diameter of the roll.

5. The method of claim 3, wherein each of the in situ mechanical wave and the reference mechanical wave propagates along the chord of the roll.

6. The method of claim 3, additionally comprising:
   transmitting a second in situ mechanical wave through the roll at the in situ temperature;
   measuring a second in situ propagation time of the second in situ mechanical wave through the roll at a second location spaced apart from the first location; and
   comparing the second in situ propagation time with the reference propagation time to determine a second amount of thermal expansion of the roll between the reference temperature and the in situ temperature.

7. The method of claim 6, wherein the measuring the in situ propagation time and the measuring the second in situ propagation time are performed by a single sensor operable to move with respect to the roll.

8. The method of claim 1, additionally comprising adjusting temperature control of the roll based on the amount of thermal expansion.

9. The method of claim 1, additionally comprising:
   comparing the in situ propagation time with the reference propagation time to determine an average temperature of the roll at the in situ temperature.

10. The method of claim 1, further comprising measuring the reference temperature of the roll.

11. The method of claim 10, wherein comparing the in situ propagation time with the reference propagation time to determine the amount of thermal expansion of the roll includes using the reference temperature of the roll.

12. The method of claim 11, further comprising determining a speed of sound through the roll at the reference temperature, wherein comparing the in situ propagation time with the reference propagation time to determine the amount of thermal expansion of the roll includes using the speed of sound through the roll at the reference temperature.

* * * * *